(12) United States Patent
Danno et al.

(10) Patent No.: US 8,237,926 B2
(45) Date of Patent: Aug. 7, 2012

(54) METHOD AND APPARATUS FOR MEASURING DENSITY

(75) Inventors: Minoru Danno, Kanagawa (JP); Kenji Muta, Kanagawa (JP); Masazumi Tanoura, Kanagawa (JP); Masatoshi Katsuki, Kanagawa (JP); Yuuko Ujihara, Kanagawa (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 12/922,898

(22) PCT Filed: Apr. 15, 2009

(86) PCT No.: PCT/JP2009/057949
§ 371 (c)(1),
(2), (4) Date: Oct. 6, 2010

(87) PCT Pub. No.: WO2010/050255
PCT Pub. Date: May 6, 2010

(65) Prior Publication Data
US 2011/0019193 A1    Jan. 27, 2011

(30) Foreign Application Priority Data
Oct. 29, 2008  (JP) .................. 2008-278798

(51) Int. Cl.
*G01N 21/00* (2006.01)
(52) U.S. Cl. .................................. 356/433
(58) Field of Classification Search .......... None
See application file for complete search history.

(56) References Cited

U.S. PATENT DOCUMENTS

| 4,981,362 A * | 1/1991 | deJong et al. ............... 356/436 |
| 6,274,879 B1* | 8/2001 | Best-Timmann ............ 250/573 |
| 6,315,955 B1 | 11/2001 | Klein |
| 2006/0262311 A1 | 11/2006 | Muta et al. |
| 2009/0229250 A1 | 9/2009 | Yamakage et al. |

FOREIGN PATENT DOCUMENTS

| CN | 1659428 | 8/2005 |
| CN | 101216409 | 7/2008 |
| EP | 1 647 820 | 4/2006 |
| JE | 2004-219379 | 8/2004 |
| JP | 60-100033 | 6/1985 |
| JP | 3185310 | 8/1993 |
| JP | 8-285766 | 11/1996 |
| JP | 10-185814 | 7/1998 |
| JP | 2001-74654 | 3/2001 |

(Continued)

OTHER PUBLICATIONS

International Search Report issued Jul. 21, 2009 in International (PCT) Application No. PCT/JP2009/057949.

(Continued)

*Primary Examiner* — Tu Nguyen
(74) *Attorney, Agent, or Firm* — Wenderoth, Lind & Ponack, L.L.P.

(57) ABSTRACT

A method and apparatus for measuring density which can simultaneously measure gaseous substance density and solid particulate material density and further can simultaneously measure the densities of a plurality of materials such as black smoke, white smoke, and water vapor. The method includes irradiating a laser having at least one wavelength equivalent to an absorption wavelength of each gaseous substance to be measured.

20 Claims, 6 Drawing Sheets

FOREIGN PATENT DOCUMENTS

| | | |
|---|---|---|
| JP | 2004-219379 | 8/2004 |
| JP | 2005-24251 | 1/2005 |
| JP | 2005-106546 | 4/2005 |
| SU | 1 676 335 | 5/1996 |
| WO | 2007/077966 | 7/2007 |

OTHER PUBLICATIONS

Chinese Office Action (with English translation) issued Oct. 18, 2011 in the corresponding Chinese Patent Application No. 200980111302.3.

International Preliminary Report on Patentability and Written Opinion of the International Searching Authority (in English), issued May 12, 2011 in International Application No. PCT/JP2009/057949.

Russian Office Action (together with English translation) issued Oct. 21, 2011 in corresponding Russian Patent Application No. 2010140055/28(057290).

Decision on Grant (with English translation) issued Feb. 21, 2012 in corresponding Russian Application No. 2010140055/28.

* cited by examiner

METHOD AND APPARATUS FOR MEASURING DENSITY

BACKGROUND OF THE INVENTION

1. Field of the Invention

The present invention relates to a measuring method and device for measuring density as to a gaseous substance and a particulate matter in a gas which is a gas generated in a closed vessel such as a boiler, a refuse incinerator, and a combustion chamber of combustion engine, a gas that is emitted outward from the closed vessel or the emitted gas that is prone to stay around a gas flow stagnation area.

2. Background of the Invention

The methods by use of laser technologies for measuring the density of the gaseous substances and particulate matters in the gas have been conventionally developed whereby the gas is generated in a closed vessel such as a combustion chamber for a boiler, a refuse incinerator, a combustion engine and so on. The gas density measuring technologies by use of laser make use of the property of each kind of gaseous substances; namely, a gaseous substance has the property of absorbing a laser having a component of a wavelength peculiar to the gaseous substance. In other words, the density of a specific gaseous substance is identified by applying a laser including the specific wavelength equivalent to the absorption wavelength peculiar to the gaseous substance toward the measurement object gas containing the gaseous substance, and performing spectrum analysis regarding the laser that passes through the measurement object gas.

It is, hereby, noted that the term "laser" in this specification mainly relates to the lasers that emit a broad spectrum of light, or emit different wavelengths of light simultaneously.

On the other hand, as for the measurement of the density of a particulate matter suspending in the measurement object gas, a method has been conventionally made use of, whereby a predetermined amount of the gas containing the particulate matter is taken as a sample for analysis; the sampled amount of the gas is passed through a filter paper (e.g. a filter paper placed in a cylinder strainer); the difference between the weight of the paper filter after the sampled amount of the gas is passed through the filter paper and the weight of the paper filter before the sampled amount of the gas is passed through the filter paper is estimated so that the particulate matter in the predetermined amount of the sampled gas.

As an example method described above, the patent reference 1 (JP1998-185814) discloses a method for measuring density as to a gaseous substance and a particulate matter by use of the laser technology; namely, the patent reference 1 discloses a density measuring device for simultaneously measuring the densities as to a gaseous substance and a particulate matter, by applying the laser corresponding to the special absorption wavelength peculiar to the gaseous substance, toward the measurement object gas (the gas and the particulate matter therein). In the technology of the patent reference 1, as shown in FIG. 9, the base attenuation Ap regarding the base laser transmittance (transmissivity) corresponds to the attenuation due to the particulate matter; the peak attenuation (absorption) Ag of a sharp valley shape corresponds to the attenuation due to the gaseous substance; thus, the density of the particulate matter can be computed by use of the measured value Ap, while the density of the gaseous substance can be computed by use of the measured value Ag.

Further, the patent reference 2 (JP Patent 3185310) discloses a smoke detector for detecting the smoke emitted from a traveling car (or vehicle); according to the disclosed technology, the to-be-detected smoke may be black smoke, white smoke, water vapor or mixture of white smoke and water vapor; a part of the light (laser) outputted from the laser emitting means is scattered or reflected in the measurement object gas containing the particulate matters; a part of the light is received by a plurality of laser receiving means; according to the light reception conditions of the laser receiving means, the state (such as density information) of the smoke (black smoke, white smoke, water vapor or mixture of white smoke and water vapor) can be estimated.

As described above, the patent reference 1 discloses a density-measuring device that simultaneously measures both densities regarding the gaseous substance and the particulate matter; however, the density regarding the particulate matter is estimated as one overall value; the technology according to the patent reference 1 does not make a distinction among particulate matters in black smoke, white smoke and water vapor; the technology does not reach a level where the density regarding the particulate matter in each smoke can be separately measured. Hereby, it is noted that black smoke, white smoke and water vapor (steam white smoke) mean black smoke containing black solid particulates, white smoke containing liquid particulates and water vapor containing water particulates, respectively.

Further, in the technology according to the patent reference 2, the particulate matter in each smoke such as black smoke, white smoke, or water vapor is measured only independently; the densities regarding the particulate matter and the specific gaseous substance such as $NH_3$ (ammonia) or NOx (nitrogen oxide) in emission gases cannot be simultaneously measured.

DISCLOSURE OF THE INVENTION

In view of the above-described background, the present invention aims at providing a density-measuring device that can simultaneously measure both densities regarding a plurality of gaseous substances and a plurality of particulate matters whereby the device can easily and surely measure the densities regarding the particulate matters such as black smoke, white smoke and water vapor; further, the present invention aims at providing a density-measuring method in response to the device.

In order to overcome the problems in the conventional technologies, the first invention of the present application is a density measuring method for detecting densities of gaseous substance and particulate matter in a measurement object gas containing the gaseous substance and the particulate matter on a basis of transmittance and attenuation of a laser measured by irradiating the laser including a wavelength equivalent to an absorption wavelength peculiar to the gaseous substance through the measurement object gas; the method comprising steps of:

establishing a relation between laser attenuation and a density of each particulate matter such as black smoke or white smoke in response to each absorption wavelength peculiar to each gaseous substance in advance;

irradiating laser having at least one wavelength equivalent to each gaseous substance to be measured; and determining the density of each particulate matter by measuring the laser attenuation in response to the wavelength of the laser, and comparing the measured attenuation with the attenuation computed by use of the relation established in advance.

The second invention of the present application is density measuring device for detecting densities of gaseous substance and particulate matter in a measurement object gas containing the gaseous substance and the particulate matter on a basis of transmittance and attenuation of a laser measured by irradiating the laser including a wavelength equivalent to an absorption wavelength peculiar to the gaseous substance through the measurement object gas; the device comprising:

at least one laser emitting means that irradiates the laser including at least one wavelength equivalent to the absorption wavelength peculiar to each gaseous substance to be measured;

at least one laser receiving means that receives the laser irradiated by the laser emitting means;

a laser attenuation coefficient map in which a relation between laser attenuation and a density of each particulate matter such as black smoke or white smoke in response to each absorption wavelength peculiar to each gaseous substance is established in advance;

at least one laser attenuation computing means that computes the attenuation of the laser having passed through the measurement object gas on the basis of the laser received by the laser receiving means; and a particulate matter density computation means that computes the density regarding each particulate matter by comparing the attenuation computed by the laser attenuation computing means with the attenuation computed by use of an attenuation coefficient of the laser attenuation coefficient map.

According to the first and second inventions, lasers including wavelengths equivalent to absorption wavelengths peculiar to the gaseous substances are irradiated through the measurement object gas; a laser attenuation coefficient map in which the relation between the attenuation and the density of each particulate matter such as black smoke or white smoke is predeterminately established in response to each absorption wavelength peculiar to each gaseous substance; the attenuation in response to the wavelength of the laser is measured; and, the measured attenuation is compared with the attenuation that is computed by use of the established relation between the attenuation and the density of each particulate matter such as black smoke or white smoke, so that the density of each particulate matter is determined. Thus, the densities regarding particulate matters such as black smoke, white smoke and so on in the density-measurement object gas can be detected at the same time.

More concretely, for instance, the laser including wavelength $\lambda_1$ is assumed to be the laser for detecting the density of CO (carbon monoxide) included in the measurement object gas; further, for instance, the laser including wavelength $\lambda_2$ is assumed to be the laser for detecting the density of ammonia $NH_3$ (ammonia) included in the measurement object gas; thereby, an attenuation coefficient "a" for black smoke with respect to the laser of the wavelength $\lambda_1$ and an attenuation coefficient "b" for white smoke with respect to the laser of the wavelength $\lambda_1$ are predetermined; further, an attenuation coefficient "c" for black smoke with respect to the laser of the wavelength $\lambda_2$ and an attenuation coefficient "d" for white smoke with respect to the laser of the wavelength $\lambda_2$ are predetermined. Incidentally, these attenuation coefficients are established as shown in FIGS. 4 and 5 that give explanation about a map (a registered relationship graph between laser attenuation and smoke density) of laser attenuation regarding black smoke and white smoke, respectively.

Further, the laser attenuation $A_{\lambda,1}$ regarding the laser of the wavelength $\lambda_1$ and the laser attenuation $A_{\lambda,2}$ regarding the laser of the wavelength $\lambda_2$ can be expressed in the following equations (1) and (2), with respect to the black smoke density $N_b$ and the white smoke density $N_w$. In other word, the attenuations $A_{\lambda,1}$ and $A_{\lambda,2}$ can be primary expressions regarding the densities $N_b$ and $N_w$.

$$A_{\lambda,1} = aN_b + bN_w \quad (1)$$

$$A_{\lambda,2} = bN_b + dN_w \quad (2)$$

Thus, the black smoke density $N_b$ and the white smoke density $N_w$ can be obtained by solving the simultaneous equations (1) and (2) with respect to the unknowns $N_b$ and $N_w$. In addition, either of the laser attenuation $\lambda_{\lambda,1}$ regarding the laser of the wavelength $\lambda_1$ and the laser attenuation $A_{\lambda,2}$ regarding the laser of the wavelength $\lambda_2$ is computed on the basis of the laser intensity signal in response to the intensity of each laser that is received at each laser receiving means.

Thus, according to the first and second inventions, by irradiating the lasers through the density-measurement object gas, the densities regarding particulate matters in the density-measurement object gas can be simply and surely computed at the same time, on the basis of the laser attenuation corresponding to each laser of its own wavelength.

An preferable embodiment according to the first invention is the density measuring method further comprising steps of:

irradiating the laser not only through the measurement object gas but also through a reference cell in which a reference gas made from the gaseous substance is encapsulated; and identifying the attenuation as a measured attenuation on the basis of an intensity signal corresponding to the intensity of the laser having passed through the reference cell and a transmittance intensity signal corresponding to the transmittance intensity of the laser having passed through the measurement object gas An preferable embodiment according to the second invention is a density measuring device, wherein the laser is irradiated not only through the measurement object gas but also through a reference cell in which a reference gas made from the gaseous substance is encapsulated, and the attenuation of the laser including at least one wavelength equivalent to the absorption wavelength peculiar to each gaseous substance to be measured is computed on the basis of an intensity signal corresponding to the intensity of the laser having passed through the reference cell and a transmittance intensity signal corresponding to the transmittance intensity of the laser having passed through the measurement object gas.

According to the configuration of each invention as described above, each laser attenuation in response to each laser absorption wavelength is computed on the basis of the intensity signal corresponding to the intensity of the laser having passed through the reference gas and the intensity signal corresponding to the transmittance intensity of the laser having passed through the measurement object gas; therefore, the density measurement can be prevented from being influenced by the fluctuations as to each laser intensity on the laser emitting side.

Another preferable embodiment according to the first invention is a density measuring method further comprising steps of:

irradiating the laser not only through the measurement object gas but also through a reference cell in which a reference gas made from the gaseous substance is encapsulated; and locking the wavelength of the laser irradiated through the measurement object gas to an absorption wavelength of the reference gas encapsulated in the reference cell on the basis of an electrical signal of the laser having passed through the corresponding reference cell.

Another preferable embodiment according to the second invention is a density measuring device, wherein the laser emitted by the laser emitting means is irradiated not only through the measurement object gas but also through a reference cell in which a reference gas made from the gaseous substance is encapsulated; and the wavelength of the laser irradiated through the measurement object gas is locked to an absorption wavelength of the reference gas encapsulated in the reference cell on the basis of an electrical signal of the laser having passed through the corresponding reference cell.

According to the configuration of each invention as described above, by irradiating the laser including the wavelength equivalent to the absorption wavelength peculiar to each gaseous substance, through a reference cell encapsulated with a reference gas made from the gaseous substance, as well as by locking the wavelength of the laser irradiated through the measurement object gas to the absorption wavelength of the reference gas, the laser emitted from the laser emitting means can include wavelength components of less deviation (around the absorption wavelength); thus, the measurement accuracy deterioration due to the wavelength deviation can be constrained.

Another preferable embodiment according to the first invention is a density measuring method, wherein the method is further provided with a wavelength modulation means and a wavelength demodulation means, the method comprising steps of:

irradiating a plurality of lasers including at least one wavelength equivalent to the absorption wavelength peculiar to each gaseous substance to be measured; and measuring the density of each gaseous substance in the measurement object gas based on absorption of the gaseous substance as to each absorption wavelength.

Another preferable embodiment according to the second invention is a density measuring device comprising a wavelength modulation means and a wavelength demodulation means, wherein a plurality of lasers including at least one wavelength equivalent to the absorption wavelength peculiar to each gaseous substance to be measured are irradiated by the laser emitting means, and the density of each gaseous substance in the measurement object gas is measured based on absorption of the gaseous substance as to each absorption wavelength According to the configuration of each invention as described above, the densities as to a plurality of gaseous substances can be measured at the same time; more concretely, the densities as to a plurality of particulate matters such as black smoke, white smoke, water vapor can be measured at the same time, while the densities as to a plurality of gaseous substances can be measured. Thus, the efficiency as to the exhaust gas analysis can be enhanced.

According to the present invention, a measuring method and a device for measuring the density as to a plurality of gaseous substances and particulate matters in a measurement gas can be realized; thereby, the measurement gas including the gaseous substances and the particulate matters is generated in a closed vessel such as a combustion chamber for a boiler, a refuse incinerator, a combustion engine and so on, the gas being emitted outward from the closed vessel; the densities as to the gaseous substances and the densities as to the particulate matters can be measured at the same time; in addition, the densities as to a plurality of particulate matters such as black smoke, white smoke and water vapor are surely measured in a simple way at the same time.

DETAILED DESCRIPTION OF THE PREFERRED EMBODIMENTS

Hereafter, the present invention will be described in detail with reference to the embodiments shown in the figures. However, the dimensions, materials, shape, the relative placement and so on of a component described in these embodiments shall not be construed as limiting the scope of the invention thereto, unless especially specific mention is made.

First Embodiment

Figure 1:
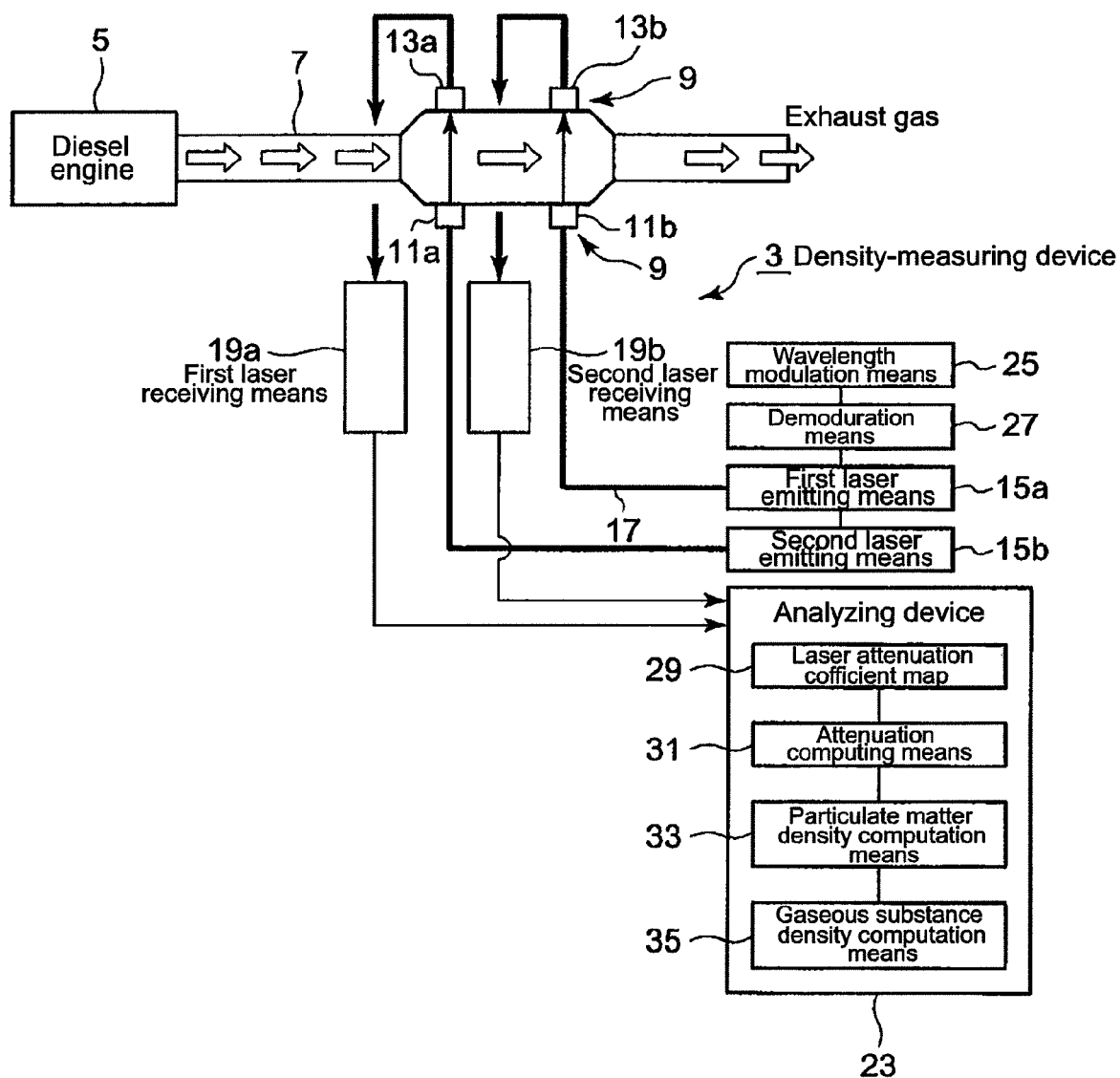
FIG. 1 shows a whole configuration as to the density-measuring device which is applied to a diesel engine for performing an exhaust gas analysis according to the present invention.

FIG. 1 shows a density-measuring device 3 applied to an exhaust gas analysis of a diesel engine 5, according to a first embodiment of the present invention.

An exhaust gas passage 7 of the diesel engine 5 is provided with a measuring sensor unit 9 in which a plurality of lasers (two lasers in this example) are irradiated so that the lasers irradiated across the exhaust gas passage 7. The measuring sensor unit 9 is provided with collimators (optical lens) 11a and 11b to a laser emitting side and collimators (optical lens) 13a and 13b to a laser receiving side.

The density-measuring device 3 includes a first laser emitting means 15a and a second laser emitting means 15b. Lasers emitted from these means 15a and 15b are carried to the measuring sensor unit 9 through optical fibers 17. The lasers applied in the measuring sensor unit 9 pass through the exhaust gas, and reach a first laser receiving means 19a and a second laser receiving means 19b. At these means 19a and 19b, the lasers are converted into electronic signals that are inputted into an analyzing device 23 for analyzing the density of the gaseous substance and the particulate matter. Further, the density-measuring device 3 is provided with a wavelength modulation means 25 and a demodulation means 27, and the analyzing device 23 is provided with a laser attenuation coefficient map 29, an attenuation computing means 31, a particulate matter density computation means 33 and a gaseous substance density computation means 35.

Figure 2:
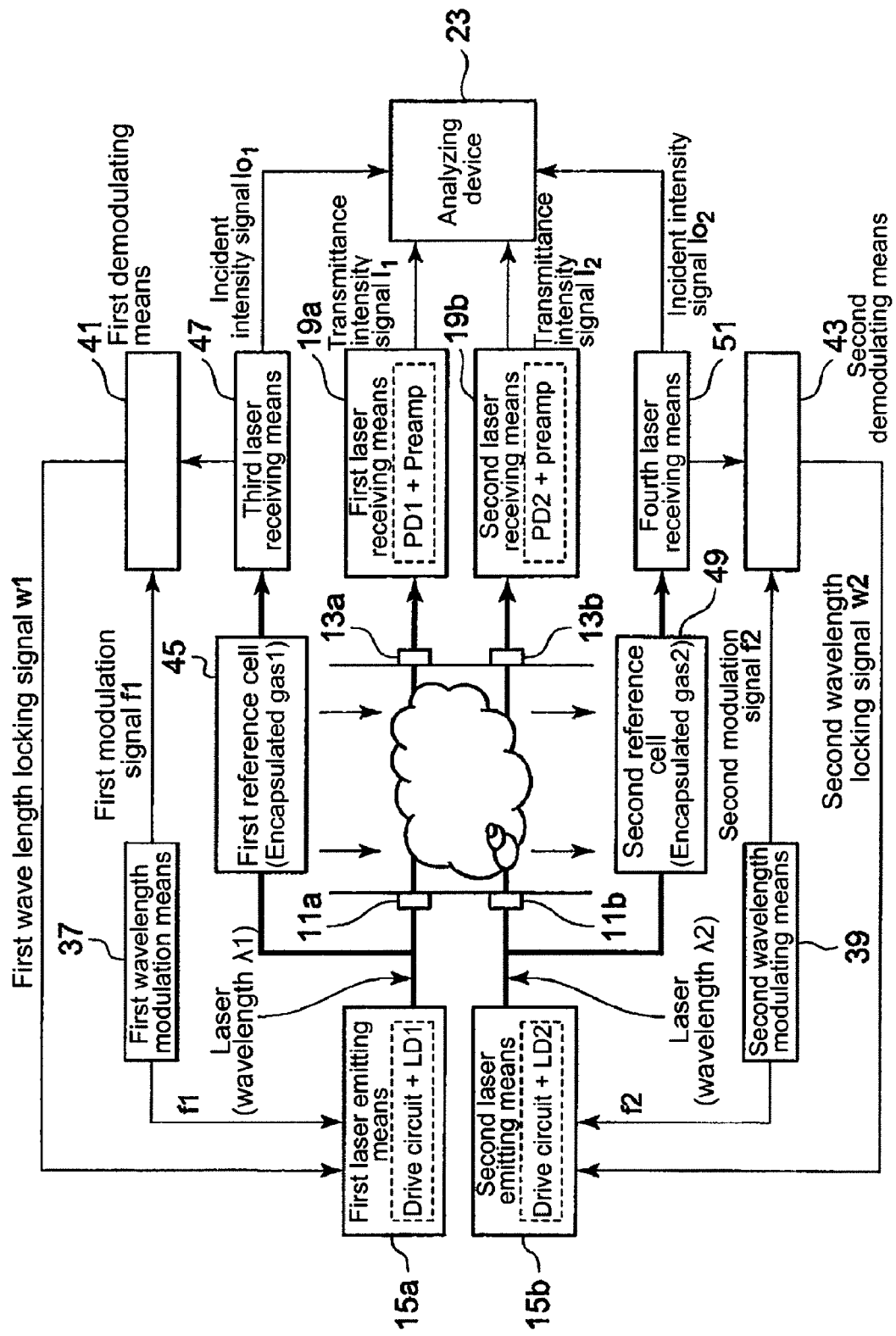
FIG. 2 shows a whole configuration as to the density-measuring device according to a first embodiment of the present invention.

As shown in FIG. 2, the first laser emitting means 15a as well as the second laser emitting means 15b configure the laser emitting source; the first laser emitting means 15a emits lasers including wavelength $\lambda_1$ while the second laser emitting means 15b emits lasers including wavelength $\lambda_2$. The laser emitting means 15a has a semiconductor laser diode LD1 and a first drive circuit therefor, while the second laser emitting means 15b has a semiconductor laser diode LD2 and a second drive circuit therefor; the semiconductor laser diode LD1 is connected to the first drive circuit that forms a LD-driver for driving the laser diode LD1, while the semiconductor laser diode LD2 is connected to the second drive circuit that forms a LD-driver for driving the laser diode LD2; the LD-driver controls the drive current passing the semiconductor diodes LD1 and LD2.

Further, toward the first drive circuit of the first laser emitting means 15a, a first modulation signal f1 is applied from a first wavelength-modulating means 37, and a first wavelength locking signal w1 is applied from a first demodulating means 41. Toward the second drive circuit of the second laser emitting means 15b, a second modulation signal f2 is applied from a second wavelength-modulating means 39, and a second wavelength locking signal w2 is applied from a second demodulating means 43.

The above-described modulation signals f1 and f2 are applied to the corresponding laser emitting means so as to perform frequency modulation regarding lasers; the modulation signal f1 is also applied to the first demodulating means 41 in order to establish a synchronizing signal that can be used for intensifying the modulation signal f1; similarly, the modulation signal f2 is also applied to the second demodulating means 43 in order to establish a synchronizing signal that can be used for intensifying the modulation signal f2.

The lasers that are received by the measuring sensor unit 9 are carried to the first laser receiving means 19a and the second laser receiving means 19b. The lasers that are carried to the first laser receiving means 19a and the second laser receiving means 19b are converted into electrical signals (that are called intensity signals herein) in response to the strength of lasers; namely, the first laser receiving means 19a and the second laser receiving means 19b output the intensity signals. The first laser receiving means 19a comprises a photodiode PD1, while the second laser receiving means 19b comprises a photodiode PD2; the photodiodes PD1 and PD2 convert the received lasers into electrical signals. Further, each of the laser receiving means 19a and 19b comprises a preamp (preamplifier) that amplifies the converted electrical signals. The intensity signals outputted at the first laser receiving means 19a or the second laser receiving means 19b are decomposed into DC (direct-current) components and AC (alternating-current) harmonic components, by use of DC component detecting means (not shown) and AC component detecting means (not shown); the decomposed DC component corresponds to the attenuation Ap (the base attenuation Ap in FIG. 9) regarding the laser transmittance; the attenuation Ap is attributable to the particulate matter and the density thereof; the signal regarding the DC component is inputted into the analyzing device 23 as a transmittance intensity signal $I_1$ (for the first laser receiving means 19a) or $I_2$ (for the second laser receiving means 19a).

Meanwhile, the laser emitted from the first laser emitting means 15a are demultiplexed by a demultiplexer and carried into a first reference cell 45 in which a reference gas under a certain level of pressure is encapsulated; thereby, the properties of the encapsulated gas are to be already known. The laser carried into the first reference cell 45 passes through the encapsulated gas and are received by a third laser receiving means 47, in which the intensity of the laser is converted into electrical signals, and then the electrical signals are converted by the third laser receiving means 47 to be inputted into the first demodulating means 41. Further, into the first demodulating means 41, the first modulation signal f1 is inputted from the first wavelength-modulating means 37, and synchronizing signals that synchronizes to the first modulation signal f1 are produced out of the electrical signals converted by the third laser receiving means 47, at the first demodulating means 41; and, the absorption wavelength of the laser that is absorbed in the encapsulated gas in the reference cell is accurately detected. The detected absorption wavelength is peculiar to the kind of the encapsulated gas. Further, the first wavelength locking signal w1 is transmitted from the first demodulating means 41 toward the drive circuit in the first laser emitting means 15a, so that the laser diode LD1 in the first laser emitting means 15a oscillates the laser of the absorption wavelength.

Likewise, the explanation analogous to the above can be given as to the laser that is emitted from the second laser emitting means 15b and is carried into a second reference cell 49 shown in FIG. 2. The laser carried into the second reference cell 49 passes through the encapsulated gas and are received by a fourth laser receiving means 51, in which the intensity of the laser is converted into electrical signals. The electrical signals converted by the fourth laser receiving means 51 are inputted into the second demodulating means 43. Further, into the second demodulating means 43, the second modulation signal f2 is inputted from the second wavelength-modulating means 39, and synchronizing signals that synchronizes to the second modulation signal f2 are produced out of the electrical signals converted by the fourth laser receiving means 51, at the second demodulating means 43. Further, the second wavelength locking signal w2 is transmitted from the second demodulating means 43 toward the drive circuit in the second laser emitting means 15b, so that the laser diode LD2 in the second laser emitting means 15b oscillates the laser beams of the absorption wavelength.

Figure 3:
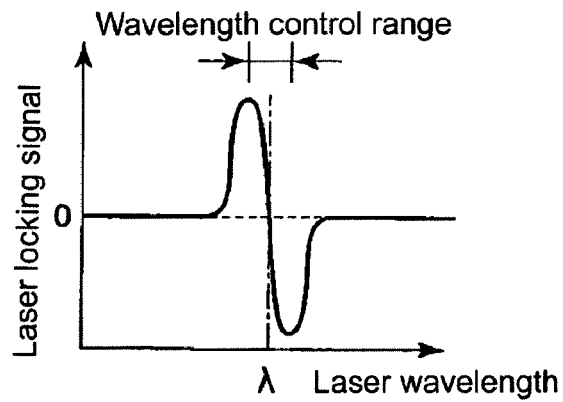
FIG. 3 is an explanatory drawing illustrating a wavelength-locking signal.

Incidentally, in the first reference cell 45, carbon monoxide (CO), for instance, as a reference gas to be measured is encapsulated; and, in the second reference cell 49, ammonia ($NH_3$), for instance, as a reference gas to be measured is encapsulated. The accurate wavelength $\lambda_1$ is detected by use of the first reference cell 45, while the accurate wavelength $\lambda_2$ is detected by use of the second reference cell 49; and, the wavelength locking signals w1 and w2 are outputted. FIG. 3 shows a concrete example as to the wavelength-locking signal with respect to the laser wavelength; the modulation is performed within a wavelength control range as shown, in FIG. 3.

Further, the intensity of the electrical signal outputted by the third laser receiving part means 47 is regarded as an incident intensity signal $I_{01}$, while the intensity of the electrical signal outputted by the fourth laser receiving part means 51 is regarded as an incident intensity signal $I_{02}$; and, both the signals $I_{01}$ and $I_{02}$ are inputted into the analyzing device 23.

The density analysis performed in the analyzing device 23 is explained as follows.

Figure 4:
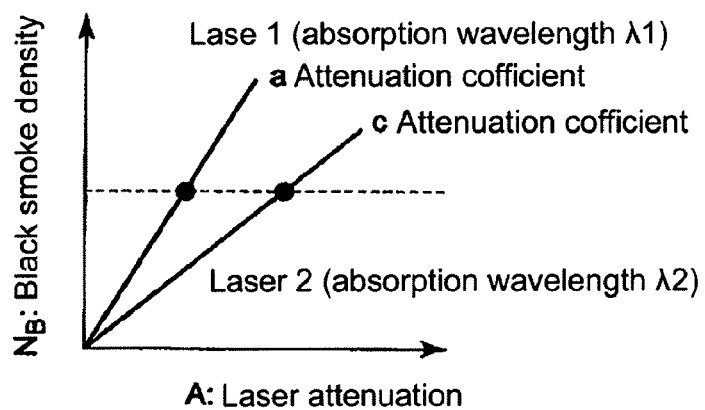
FIG. 4 is an explanatory drawing illustrating a map of laser attenuation regarding black smoke.
Figure 5:
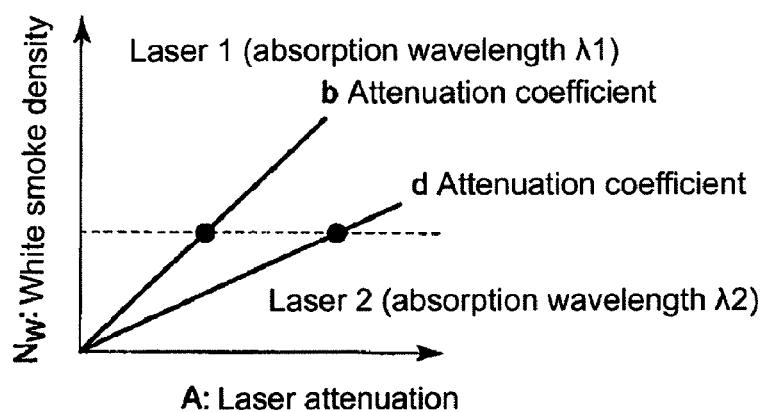
FIG. 5 is an explanatory drawing illustrating a map of laser attenuation coefficient regarding white smoke.

As shown in FIGS. 4 and 5, the analyzing device 23 (cf. FIG. 1) is provided with a laser attenuation coefficient map 29 (a registered relationship between laser attenuation and smoke density). FIG. 4 gives an explanation about a map of laser attenuation regarding black smoke; for instance, in order to identify the density of CO (carbon monoxide) included in a gas, an attenuation coefficient "a" regarding a laser including wavelength $\lambda_1$ as well as an attenuation coefficient "c" regarding a laser including wavelength $\lambda_2$ is established in FIG. 4, both the attenuation coefficients "a" and "c" being established in relation to the attenuation regarding black smoke. Further, in FIG. 4, each of the attenuation coefficients "a" and "c" is established as a linear function or a substantially linear function with respect to the laser attenuation.

On the other hand, FIG. 5 gives an explanation about a map of laser attenuation regarding white smoke; for instance, in order to identify the density of CO (carbon monoxide)

included in a measuring object gas, an attenuation coefficient "b" regarding a laser including wavelength $\lambda_1$ as well as an attenuation coefficient "d" regarding a laser including wavelength $\lambda_2$ is established in FIG. 5, both the attenuation coefficients "b" and "d" being established in relation to the attenuation regarding white smoke. Further, in FIG. 5, each of the attenuation coefficients "b" and "d" is established as a linear function or a substantially linear function with respect to the laser attenuation.

Further, the following equations (1) and (2) hold as to the laser attenuation $A_{\lambda 1}$ regarding the wavelength $\lambda_1$ as well as the laser attenuation $A_{\lambda 2}$ regarding the wavelength $\lambda_2$ under a coexistence condition of black smoke and white smoke. Here, the density of the black smoke is $N_b$ and the density of the white smoke is $N_w$.

$$A_{\lambda 1} = aN_b + bN_w \quad (1)$$

$$A_{\lambda 2} = bN_b + dN_w \quad (2)$$

Thus, the black smoke density $N_b$ and the white smoke density $N_w$ can be obtained by solving the simultaneous equations (1) and (2) with respect to the unknowns $N_b$ and N.

The laser attenuation $A_{\lambda 1}$ regarding the wavelength $\lambda_1$ as well as the laser attenuation $A_{\lambda 2}$ regarding the wavelength $\lambda_2$ is computed by use of the attenuation computing means 31 in which $A_{\lambda 1}$ and $A_{\lambda 2}$ are computed by use of the following formula:

$$A_{\lambda 1} = -\mathrm{Log}(I_1/I_{01})$$

and $$A_{\lambda 2} = -\mathrm{Log}(I_2/I_{02}),$$

where $I_{01}$ is the incident intensity signal outputted by the third laser receiving means 47, $I_{02}$ is the incident intensity signal outputted by the third laser receiving means 51, $I_1$ is the transmittance intensity signal that means the intensity of the laser received by the first laser receiving means 19a, and $I_2$ is the transmittance intensity signal that means the intensity of the laser received by the second laser receiving means 19b. It is noted that the computation as to the values $A_{\lambda 1}$ and $A_{\lambda 2}$ is performed on the basis of the electrical intensity signals outputted by a plurality of the laser receiving means that actually receive the lasers and convert the laser intensities into electrical signals.

Incidentally, the computations for solving the black smoke density $N_b$ and the white smoke density $N_w$ by use of the equations (1) and (2) are performed by the particulate matter density computation means 33 that is provided in the analyzing device 23.

Further, as is the above-described case with the density computation as to the black smoke and white smoke, in a case where the density regarding solid particulate matter of water vapor is to be additionally identified, attenuation coefficient for each of the black smoke, white smoke and water vapor as to the wavelength $\lambda_1$, $\lambda_2$ and $\lambda_3$ are set in advance, and the following equations (3), (4) and (5) in which the density of the water vapor ($N_s$) is included to the equations (1) and (2) are used:

$$A_{\lambda 1} = aN_b + bN_w + eN_s \quad (3),$$

$$A_{\lambda 2} = cN_b + dN_w + fN_s \quad (4),$$

and $$A_{\lambda 3} = gN_b + hN_w + iN_s \quad (5),$$

hereby, the attenuation coefficients a, c and g relate to the black smoke; the attenuation coefficients b, d and h relate to the smoke; the attenuation coefficients e, f and i relate to the water vapor; and, Thus, the black smoke density $N_b$, the white smoke density $N_w$ and the water vapor density $N_s$ can be obtained by solving the simultaneous equations (3) to (5) with respect to the unknowns $N_b$, $N_1$ and $N_s$.

Incidentally, the attenuation coefficient e is an attenuation coefficient that represents the relation between the black smoke density and the laser attenuation, in relation to the laser including wavelength $\lambda_3$ that passes through the measurement object gas. The attenuation coefficient f is an attenuation coefficient that represents the relation between the white smoke density and the laser attenuation, in relation to the laser including wavelength $\lambda_3$ that passes through the measurement object. The attenuation coefficient g is an attenuation coefficient that represents the relation between the water vapor density and the laser attenuation, in relation to the laser including wavelength $\lambda_1$ that passes through the measurement object gas. The attenuation coefficient h is an attenuation coefficient that represents the relation between the water vapor density and the laser attenuation, in relation to the laser including wavelength $\lambda_2$ that passes through the measurement object gas. The attenuation coefficient i is an attenuation coefficient that represents the relation between the water vapor density and the laser attenuation, in relation to the laser including wavelength $\lambda_3$ that passes through the measurement object gas.

According to the first embodiment as described above, a plurality of lasers of the absorption wavelengths $\lambda_1$ and $\lambda_2$ in relation to gaseous substances contained in the measurement object gas is irradiated through the measurement object gas, and a plurality of the laser attenuation coefficients for each of the absorption wavelengths regarding particulate matters such as black smoke and white smoke is established in advance so as to predetermine the attenuation coefficients on the basis of already known information and establish them in the laser attenuation coefficient map 29. Further, the attenuations $A_{\lambda 1}$ and $A_{\lambda 2}$ for each of the lasers irradiated are measured, and each measured attenuation is correlated to the calculated attenuation by use of the attenuation coefficient map 29 in which the attenuation coefficients are established, so that the set of simultaneous equations with respect to the densities regarding the particulate matters such as black smoke and white smoke in the measurement object gas is solved. Thus, by solving the simultaneous equations, the densities of the particulate matters such as black smoke and white smoke can be simply and surely computed.

Further, in the embodiment as described thus far, the intensity of the lasers passing through the first reference cell 45 and the second reference cell 49 in which a reference gas of the gaseous substance to be measured is encapsulated is converted into the intensity electrical signals as an incident intensity signals $I_{01}$ or $I_{02}$. Moreover, the intensity signal of each lasers passing through the measurement object is converted into transmittance intensity signals $I_1$ or $I_2$. Based on the incident intensity signals $I_{03}$ and $I_{02}$ as well as the transmittance intensity signals $I_1$ and $I_2$, the density measurement by use of the lasers regarding the absorption wavelengths is performed; thus, the density measurement results can be free from the influence of the intensity fluctuations of the lasers on the oscillating side.

Further, while the lasers are applied toward the measurement object gas including the particulate matters or gaseous substance, the lasers are applied toward the first reference cell 45 and the second reference cell 49 in which the reference gases are encapsulated. Based on the electrical signal corresponding to the intensity of the laser passing through the first reference cell 45 or the second reference cell 49, the wavelength of the laser emitted by the first laser emitting means 15a or the second laser emitting means 15b is synchronized to (locked around) the absorption wavelength peculiar to the gas encapsulated in the first reference cell 45 or the second reference cell 49. Thus, the wavelength of the laser passing through the first reference cell 45 is locked around the absorption wavelength $\lambda_1$ of the reference gas encapsulated in the first reference cell 45 and the wavelength of the laser passing through the second reference cell 49 is locked around the absorption wavelength $\lambda_2$ of the reference gas encapsulated in the second reference cell 49; therefore, the deviation of the wavelength of each laser emitting means 15a or 15b is restrained; accordingly, the density measurement accuracy is prevented from being deteriorated due to the wavelength deviation.

Figure 6:
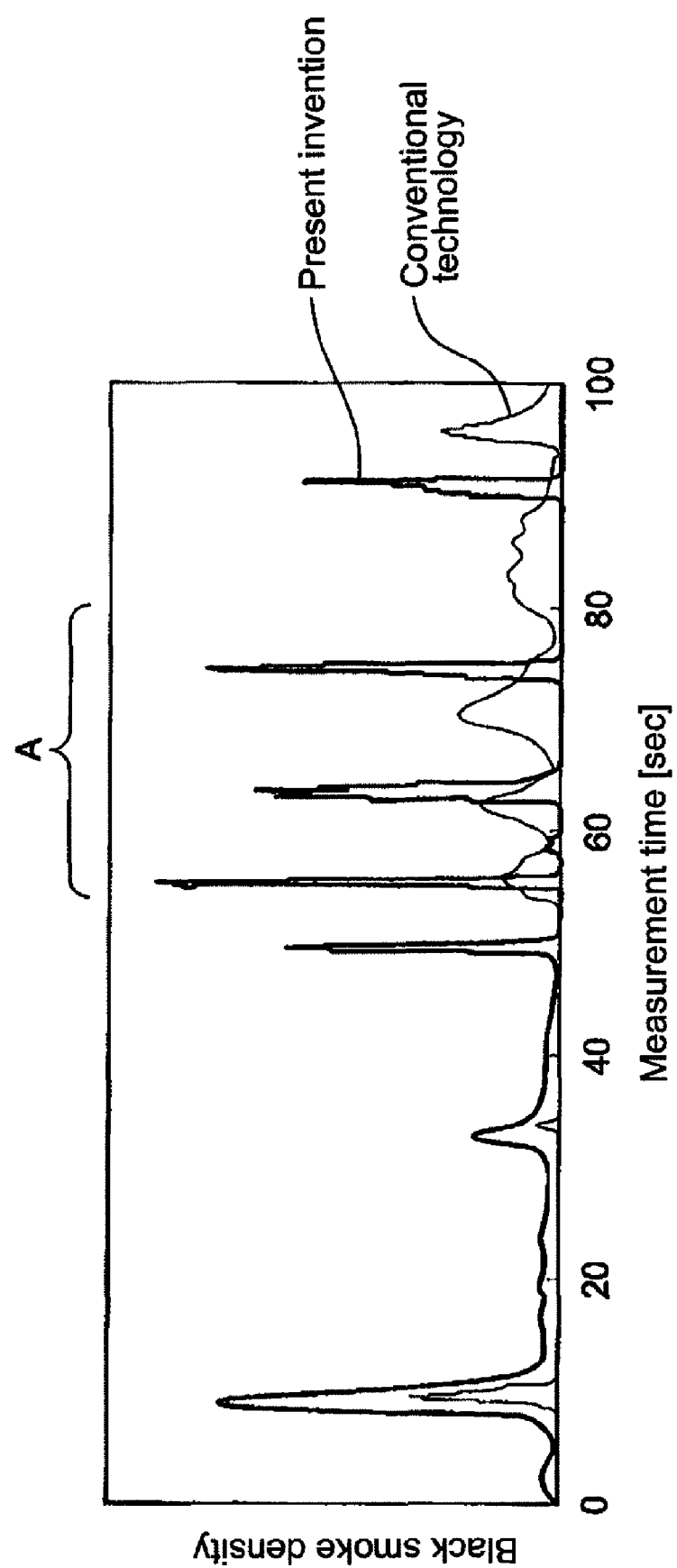
FIG. 6 is an explanatory drawing illustrating a comparison between a measured result by use of the method according to conventional technologies and a measured result by use of the method according to the present invention.

In FIG. 6, an example result as to the black smoke density measurement according to this first embodiment is compared with the measurement result according to the conventional technology, namely a gas sampling approach. As shown in the area A of FIG. 6, according to the conventional technology, the delays in measuring responses by use of conventional measuring devices are recognized, and the relaxation (i.e. being not sharp) as to the response curve is observed as well. On the contrary, according to this first embodiment, it is confirmed that the density detection with improvements in the measuring responses can be realized.

Second Embodiment

Figure 7:
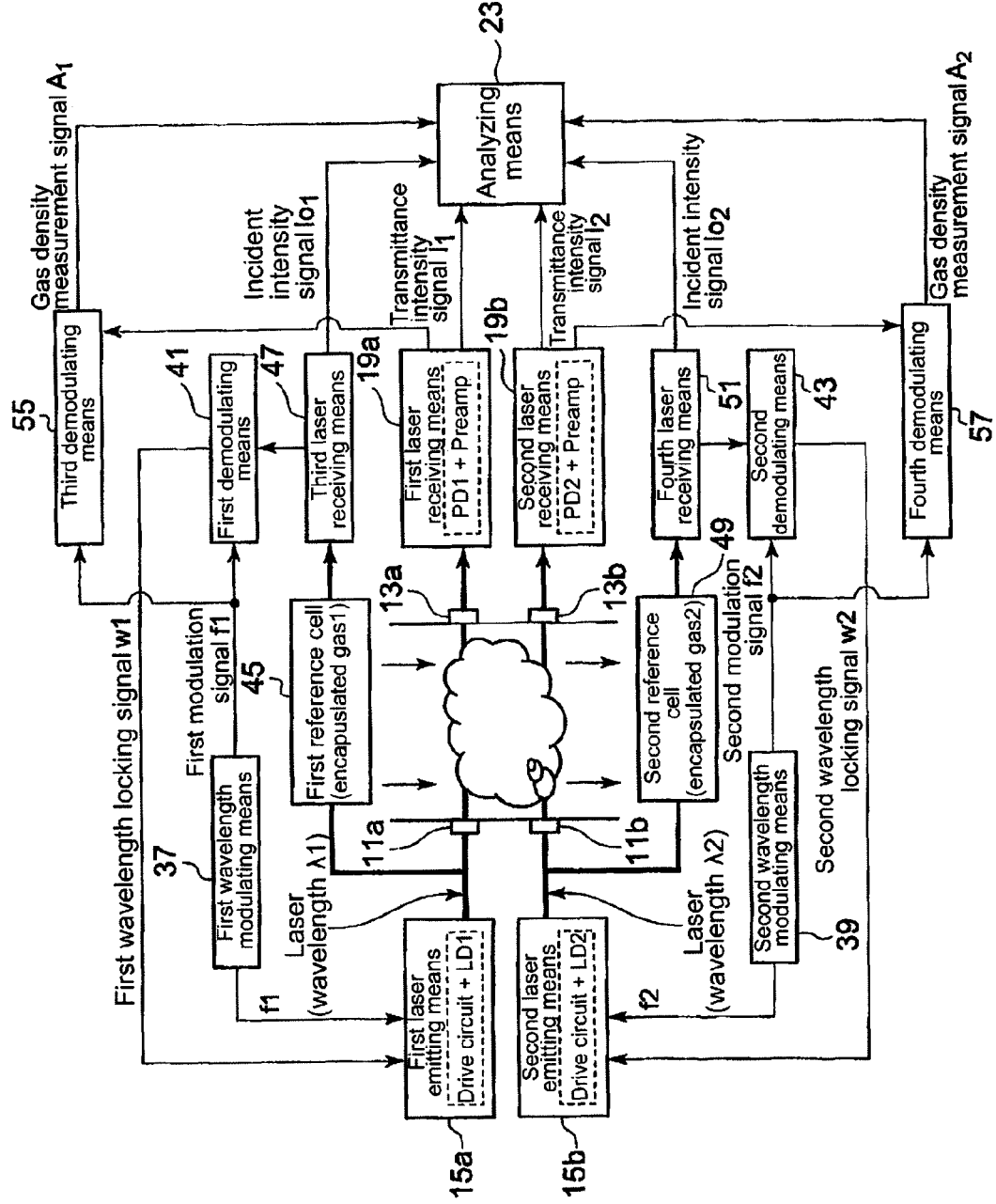
FIG. 7 shows a whole configuration as to the density-measuring device according to a second embodiment of the present invention.
Figure 8:
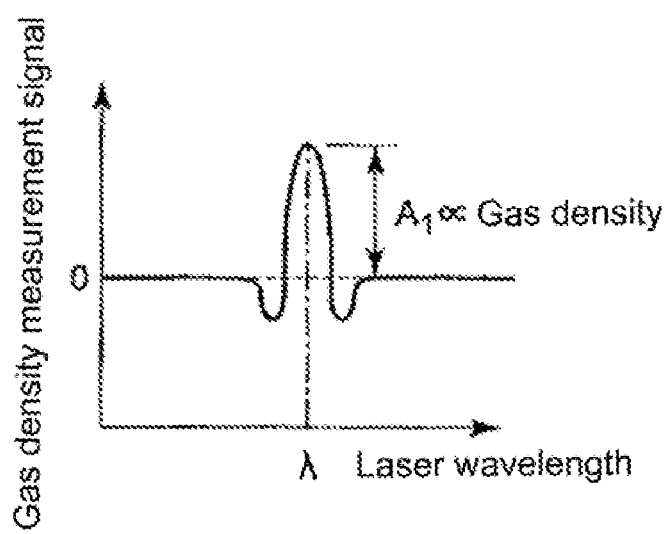
FIG. 8 is an explanatory drawing illustrating a density measurement signal regarding a gaseous substance.

Next, the second embodiment according to the present invention is explained in consultation with FIGS. 7 and 8.

In addition to the density measurement as to a plurality of particulate matters in the measurement object gas which is explained in the first embodiment, the second embodiment treats with the density measurement as to a plurality of gaseous substances in the measurement object gas; namely, the density measurement as to the particulate matter and the density measurement of the gaseous substance are performed. Incidentally, the same elements in the second embodiment as in the first embodiment are marked with the same symbols, and the explanation as to the same elements is omitted.

The whole configuration of FIG. 7 corresponds to that of FIG. 2 as per the first embodiment; in addition to the first embodiment, a third demodulating means 55, a fourth demodulating means 57 and the gaseous substance density computation means 35 (cf. FIG. 1) are provided in this second embodiment.

As explained in the first embodiment, the laser that is carried to the first laser receiving means 19a is converted into electrical signals (intensity signals) in response to the intensity of laser; namely, the first laser receiving means 19a outputs the intensity signals that are decomposed into DC (direct-current) components and AC (alternating-current) harmonic components (contents) by use of DC component detecting means (not shown) and AC component detecting means (not shown); the decomposed DC component corresponds to the attenuation Ap (the base attenuation Ap in FIG. 9) regarding the laser transmittance; the attenuation Ap is attributable to the particulate matter and the density thereof; and, the attenuation Ap is used for computing the density as to the particulate matter.

Figure 9:
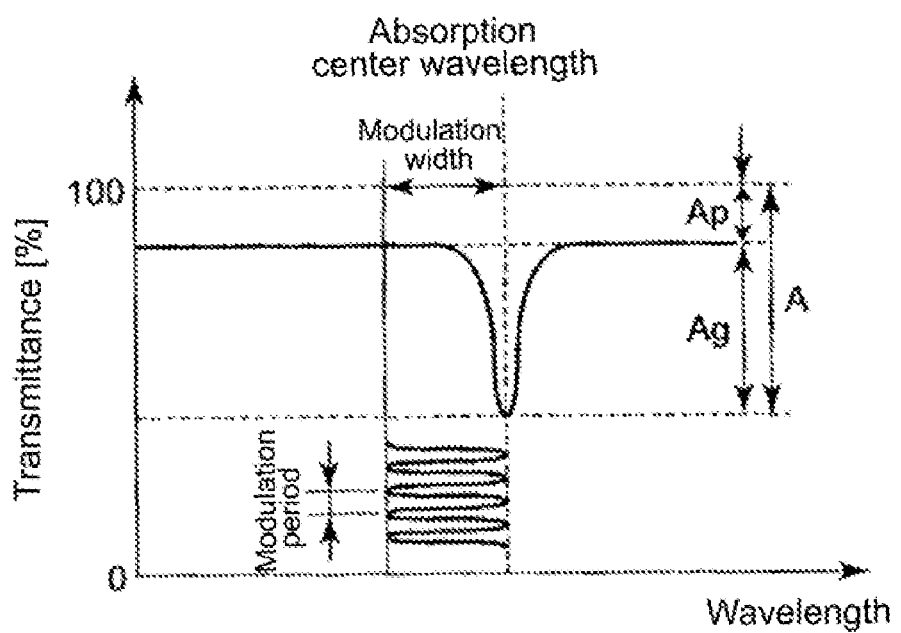
FIG. 9 is an explanatory drawing of the technical features according to the conventional technology.

On the other hand, out of the decomposed DC components, the third demodulating means 55 extracts a signal that synchronizes with the first modulation signal f1 outputted by the first wavelength-modulating means 37; the signal extracted by the third demodulating means 55 passes through a filter that removes the noises of the extracted signal described just above. Thus, the demodulating means produces a peak absorption signal in the demodulated signals. On the basis of the magnitude (size) of the peak absorption signal, the density of the gaseous substance in the measurement object gas is detected. The attenuation (absorption) Ag of the peaked shape as shown in FIG. 9 represents the attenuation attributable to the gaseous substance; hence, the density of the gaseous substance can be computed by use of the attenuation Ag. In this specification, the attenuation Ag is described as the peak attenuation.

By use of the peak (attenuation) signal $A_1$ (equivalent to the attenuation Ag as described above) that is obtained by the third demodulating means 55 and the transmittance intensity signal $I_1$ that is outputted by the first laser receiving means 19a, the density $N_{g1}$ of the gaseous substance absorbing the laser of the wavelength $\lambda_1$ is calculated by the formula $N_{g1} = \alpha_1 * A_1 / I_1$ thereby the symbol $\alpha_1$ denotes a proportional coefficient.

As is the case with the density $N_{g1}$ of the gaseous substance, the density $N_{g2}$ of the gaseous substance absorbing the laser of the wavelength $\lambda_2$ is calculated by the formula $N_{g2} = \alpha_2 \cdot A_2 / I_2$ thereby the symbol $\alpha_2$ denotes a proportional coefficient. Incidentally, the calculations as to the densities $N_{g1}$ and $N_{g2}$ are performed by the gaseous substance density computation means 35 in the analyzing device 23.

According to the second embodiment, the densities as to two kinds of gaseous substances (CO and $NH_3$) can be measured; in other words, in addition to the density measurement as to black smoke and white smoke, the density measurement as to the two kinds of gaseous substances can be performed at the same time. Thus, the efficiency as to the exhaust gas analysis of the diesel engine 5 can be enhanced.

Further, when three kinds of gaseous substances (e.g. CO, $NH_3$ and $NO_x$) are taken into consideration instead of two kinds of gaseous substances (e.g. CO, and $NH_3$), the efficiency of the density measurements as to the exhaust gas is further improved, since the density measurement as to as to a plurality of the particulate matters such as black smoke, white smoke and water vapor can be performed at the same time in parallel with the density measurement as to the gaseous substances.

In addition, it is needless to say that the number regarding the gaseous substances that can be handled at the same time is limited to neither two nor three. As a matter of course, the densities as to particulate matters of more than three kinds, if required, can be measured at the same time in parallel with the density measurement as to a plurality of gaseous substances.

In the above explanation about the first and second embodiments, the semiconductor laser diode is taken as an example of laser source; naturally, other laser oscillation devices that can perform wavelength modulation or amplitude modulation can be made use of.

INDUSTRIAL APPLICABILITY

According to the present invention, a measuring method and a device for measuring the density as to a plurality of gaseous substances and particulate matters in a measurement gas is provided; thereby, the measurement gas including the gaseous substances and the particulate matters is generated in a closed vessel such as a combustion chamber for a boiler, a refuse incinerator, a combustion engine and so on, the gas being emitted outward from the closed vessel; the densities as to the gaseous substances and the densities as to the particulate matters can be measured at the same time; in addition, the densities as to a plurality of particulate matters such as black smoke, white smoke and water vapor are surely measured in a simple way at the same time. Thus, the present invention provides a useful density measuring method and a useful density-measuring device thereof.

The invention claimed is:

1. A density measuring method for detecting densities of at least one gaseous substance and particulate matter in a measurement object gas containing the at least one gaseous substance and the particulate matter on a basis of transmittance and attenuation of a laser measured by irradiating the laser including a wavelength equivalent to an absorption wavelength peculiar to the at least one gaseous substance through the measurement object gas, the method comprising:
   establishing a relation between laser attenuation and a density of each particulate matter in response to each absorption wavelength peculiar to each gaseous substance in advance;
   irradiating a laser having at least one wavelength equivalent to an absorption wavelength peculiar to each gaseous substance to be measured; and
   determining the density of each particulate matter by measuring the laser attenuation in response to the wavelength of the laser, and comparing the measured attenuation with the attenuation computed by use of the relation established in advance.

2. The density measuring method according to claim 1, further comprising:
   irradiating the laser not only through the measurement object gas but also through a reference cell in which a reference gas made from the gaseous substance is encapsulated; and
   identifying the attenuation as a measured attenuation on the basis of an intensity signal corresponding to the intensity of the laser having passed through the reference cell and a transmittance intensity signal corresponding to the transmittance intensity of the laser having passed through the measurement object gas.

3. The density measuring method according to claim 1, further comprising:
   irradiating the laser not only through the measurement object gas but also through a reference cell in which a reference gas made from the gaseous substance is encapsulated; and
   locking the wavelength of the laser irradiated through the measurement object gas to an absorption wavelength of the reference gas encapsulated in the reference cell on the basis of an electrical signal of the laser having passed through the corresponding reference cell.

4. The density measuring method according to claim 1,
   wherein the method further comprises providing a wavelength modulation device and a wavelength demodulation device;
   wherein said irradiating operation includes irradiating a plurality of lasers including at least one wavelength equivalent to the absorption wavelength peculiar to each gaseous substance to be measured; and
   wherein the method further comprises measuring the density of each gaseous substance in the measurement object gas based on absorption of the gaseous substance as to each absorption wavelength.

5. The density measuring method according to claim 4,
   wherein the particulate matter includes black smoke and white smoke, and
   wherein the at least one gaseous substance is two gaseous substances.

6. The density measuring method according to claim 5, wherein the two gaseous substances are ammonia and carbon monoxide.

7. The density measuring method according to claim 5, wherein the particulate matter further includes water vapor.

8. The density measuring method according to claim 1,
   wherein the particulate matter includes black smoke and white smoke, and
   wherein the at least one gaseous substance is two gaseous substances.

9. The density measuring method according to claim 8, wherein the two gaseous substances are ammonia and carbon monoxide.

10. The density measuring method according to claim 8, wherein the particulate matter further includes water vapor.

11. A density measuring device for detecting densities of at least one gaseous substance and particulate matter in a measurement object gas containing the at least one gaseous substance and the particulate matter on a basis of transmittance and attenuation of a laser measured by irradiating the laser including a wavelength equivalent to an absorption wavelength peculiar to the at least one gaseous substance through the measurement object gas, the device comprising:
    at least one laser emitter that irradiates the laser including at least one wavelength equivalent to the absorption wavelength peculiar to each gaseous substance to be measured;
    at least one laser receiver that receives the laser irradiated by the laser emitter;
    an analyzing device having a laser attenuation coefficient map in which a relation between laser attenuation and a density of each particulate matter in response to each absorption wavelength peculiar to each gaseous substance is established in advance;
    at least one laser attenuation computing device that computes the attenuation of the laser having passed through the measurement object gas on the basis of the laser received by the laser receiver; and
    a particulate matter density computation device that computes the density regarding each particulate matter by comparing the attenuation computed by the laser attenuation computing device with the attenuation computed by use of an attenuation coefficient of the laser attenuation coefficient map.

12. The density measuring device according to claim 11,
    wherein the laser is irradiated not only through the measurement object gas but also through a reference cell in which a reference gas made from the gaseous substance is encapsulated, and
    the attenuation of the laser including at least one wavelength equivalent to the absorption wavelength peculiar to each gaseous substance to be measured is computed on the basis of an intensity signal corresponding to the intensity of the laser having passed through the reference cell and a transmittance intensity signal corresponding to the transmittance intensity of the laser having passed through the measurement object gas.

13. The density measuring device according to claim 11, wherein the laser emitted by the laser emitter is irradiated not only through the measurement object gas but also through a reference cell in which a reference gas made from the gaseous substance is encapsulated; and wherein the wavelength of the laser irradiated through the measurement object gas is locked to an absorption wavelength of the reference gas encapsulated in the reference cell on the basis of an electrical signal of the laser having passed through the corresponding reference cell.

14. The density measuring device according to claim 11, further comprising a wavelength modulation device and a wavelength demodulation device,
   wherein a plurality of lasers including at least one wavelength equivalent to the absorption wavelength peculiar to each gaseous substance to be measured are irradiated by the laser emitter, and the density of each gaseous substance in the measurement object gas is measured based on absorption of the gaseous substance as to each absorption wavelength.

15. The density measuring device according to claim 14, wherein the particulate matter includes black smoke and white smoke, and
   wherein the at least one gaseous substance is two gaseous substances.

16. The density measuring device according to claim 15, wherein the two gaseous substances are ammonia and carbon monoxide.

17. The density measuring device according to claim 15, wherein the particulate matter further includes water vapor.

18. The density measuring device according to claim 11, wherein the particulate matter includes black smoke and white smoke, and
   wherein the at least one gaseous substance is two gaseous substances.

19. The density measuring device according to claim 18, wherein the two gaseous substances are ammonia and carbon monoxide.

20. The density measuring device according to claim 18, wherein the particulate matter further includes water vapor.

* * * * *